United States Patent
Jiang et al.

(10) Patent No.: US 8,447,079 B2
(45) Date of Patent: May 21, 2013

(54) LINEARLY POLARIZED LIGHT IMAGING METHOD AND DEVICE

(75) Inventors: Xiaoyu Jiang, Guangdong (CN); Hui Ma, Guangdong (CN); Yonghong He, Guangdong (CN)

(73) Assignee: Graduate School at Shenzhen, Tsinghua University, Shenzhen (CN)

( * ) Notice: Subject to any disclaimer, the term of this patent is extended or adjusted under 35 U.S.C. 154(b) by 995 days.

(21) Appl. No.: 12/521,826

(22) PCT Filed: Dec. 18, 2007

(86) PCT No.: PCT/CN2007/071256
§ 371 (c)(1),
(2), (4) Date: Jun. 30, 2009

(87) PCT Pub. No.: WO2008/083573
PCT Pub. Date: Jul. 17, 2008

(65) Prior Publication Data
US 2010/0002923 A1    Jan. 7, 2010

(30) Foreign Application Priority Data

Dec. 30, 2006 (CN) .......................... 2006 1 0063723

(51) Int. Cl.
*G06K 9/00* (2006.01)
(52) U.S. Cl.
USPC ........... 382/128; 356/364; 356/367; 356/368; 356/369
(58) Field of Classification Search ... 382/128; 356/364, 356/367–369
See application file for complete search history.

(56) References Cited

U.S. PATENT DOCUMENTS

| 4,516,855 | A |   | 5/1985  | Korth |
|-----------|---|---|---------|-------|
| 4,672,196 | A | * | 6/1987  | Canino .......................... 250/225 |
| 5,005,977 | A |   | 4/1991  | Tomoff |
| 5,257,092 | A |   | 10/1993 | Noguchi et al. |

(Continued)

FOREIGN PATENT DOCUMENTS

| CN | 2819212    | 9/2006 |
| CN | 101000300  | 7/2007 |
| JP | 2004028922 | 1/2004 |

OTHER PUBLICATIONS

Steven L. Jacques et al.,"Imaging skin patology with polarized light". Journal of Biomedical Optics, Jul. 2002, vol. 7, No. 3, pp. 329-340.*
Steven L. Jacques et al., Journal of Biomedical Optics, Jul. 2002, vol. 7, No. 3, pp. 329-340.
International Search Report—PCT/CN2007/071256 filed on Dec. 18, 2007.

(Continued)

*Primary Examiner* — Matthew Bella
*Assistant Examiner* — Julian Brooks
(74) *Attorney, Agent, or Firm* — Pearne & Gordon LLP

(57) ABSTRACT

A device includes an incident arm, a detection arm, a sample stage, and an image processing computer. The incident arm includes a light source and a first polarizing element, and is disposed on one side of the sample stage. The detection arm includes a second polarizing element and a photoelectric detector, and is disposed on a light-detection path. The photoelectric detector is connected to the computer. The device further includes a device for adjusting polarization angles of the first and second polarizing elements. A method includes: illuminating a sample surface using linearly polarized light with a certain polarization angle; detecting outgoing polarized light by a photoelectric detector; adjusting polarization angles of the incident and detected polarized light, and repeating the above two steps to obtain a series of polarized images, each image corresponding to incident and detected polarization angles; and computer processing the obtained images to obtain sample information.

8 Claims, 3 Drawing Sheets

U.S. PATENT DOCUMENTS

| | | | |
|---|---|---|---|
| 5,587,793 A | 12/1996 | Nakai et al. | |
| 6,091,983 A * | 7/2000 | Alfano et al. | 600/431 |
| 6,621,578 B1 * | 9/2003 | Mizoguchi | 356/369 |
| 7,142,300 B2 * | 11/2006 | Rosengaus | 356/369 |
| 7,233,396 B1 * | 6/2007 | Hall et al. | 356/369 |
| 7,420,675 B2 * | 9/2008 | Giakos | 356/364 |

OTHER PUBLICATIONS

S. Redner, Compensation Method Using Synchronized Polarizer-Analyzer Rotation, Experimental Mechanics, Jun. 1976, pp. 221-225.

* cited by examiner

LINEARLY POLARIZED LIGHT IMAGING METHOD AND DEVICE

TECHNICAL FIELD

The present invention relates to a linearly polarized light imaging method and device, and particularly to a method and device for imaging a biological tissue based on linearly polarized light illumination, which belongs to the field of optical imaging detection technology.

BACKGROUND OF THE INVENTION

In recent years, optical detection methods have been widely used in biomedical field due to the advantages of high resolution, no damage to detected objects, and easy implementation. However, imaging depth and contrast of optical detection methods are significantly reduced by light scattering in biological tissues. Polarized light imaging methods are studied to reduce the influence of light scattering on imaging and reflect structure information of a superficial layer of a biological tissue.

It was proposed to use polarized light to image a superficial layer of a tissue to obtain birefringence information of the superficial layer of the tissue, and apply a polarized light imaging method to skin diagnosis (Journal of Biomedical Optics, July 2002, Vol. 7, No. 3). Someone has observed polarized images of normal cells and cancer cells illuminated by polarized light of different wavelengths, and proposed the possibility of identifying cancer cells with a polarized light imaging method (in Spring Topical Meetings, Optical Society of America, Orlando, Fla. (Mar. 8-11 1998)). In recent years, the polarization imaging has been applied to human tissues such as skin and blood vessels.

However, as linearly polarized light with only one polarization angle is used for illumination in the above polarization imaging methods, it is difficult to obtain overall polarization information of a biological tissue, and only the polarization information of the biological tissue can be evaluated qualitatively by the above imaging methods.

SUMMARY OF THE INVENTION

Accordingly, the present invention is directed to a linearly polarized light imaging method and device, so as to solve the problem that it is difficult to obtain overall polarization information of a biological tissue.

The present invention provides a linearly polarized light imaging device. The imaging device includes an incident arm, a detection arm, a sample stage, and an image processing computer. The incident arm includes a light source and a first polarizing element, and is disposed on one side of the sample stage. The detection arm includes a second polarizing element and a photoelectric detector, and is disposed on a light-detection path on the same or the other side of the sample stage. An output terminal of the photoelectric detector is connected to a corresponding input terminal of the computer. The imaging device further includes a polarization angle adjusting device for adjusting polarization angles of the first polarizing element and the second polarizing element.

In an embodiment of the present invention, the photoelectric detector is a two-dimensional photoelectric detector.

In an embodiment of the present invention, the imaging device further includes an optical system for generating a parallel light beam, the optical system is located behind the first polarizing element, and the parallel light beam is incident on a surface of a sample at a fixed angle.

In an embodiment of the present invention, the sample stage is a stage capable of three-dimensional movement.

In an embodiment of the present invention, the light source is a single-wavelength light source.

The present invention further provides a linearly polarized light imaging method. The imaging method includes: a) illuminating a surface of a sample to be detected using linearly polarized light with a certain polarization angle; b) recording by a photoelectric detector linearly polarized light with certain polarization angles reflected or scattered by or transmitted through the sample, that is, outgoing polarized light; c) adjusting polarization angles of the incident polarized light and the detected polarized light, and repeating the steps a) and b) to obtain a series of polarized images, each image corresponding to an incident polarization angle and a detected polarization angle; and d) processing all the obtained polarized images by a computer to obtain information of the sample to be detected.

In an embodiment of the present invention, in the step c), a method for adjusting the polarization angles of the incident polarized light and the detected polarized light includes scanning from a first angle to a second angle at a fixed interval, and a difference between the second angle and the first angle is greater than 180°.

In an embodiment of the present invention, the step d) of processing all the obtained polarized images by the computer to obtain information of the sample to be detected further includes: S2) selecting two images from the obtained polarized images, in which the two images have the same incident polarization angle, and a difference between detected polarization angles of the two images is 90°; S3) subtracting the image with a smaller detected polarization angle from the image with a larger detected polarization angle, so as to obtain a polarization-difference image at the incident polarization angle; S4) determining whether all the images have been processed or not; S5) if yes, obtaining a series of polarization-difference images corresponding to different incident polarization angles; S6) taking values of all the polarization-difference images at the same pixel; S7) fitting a functional relation of polarization differences to incident polarization angles and detected polarization angles, and extracting three particular parameters from the functional relation; S8) determining whether all pixels have been processed or not; and S9) if yes, using three particular parameters extracted at each pixel as the three color components, so as to generate a pseudo-color image.

In an embodiment of the present invention, the three particular parameters in the steps S7) and S9) are fiber orientation, anisotropy, and scattering properties of a biological tissue.

The present invention has the following advantages.

As linearly polarized light is used for area illumination of the biological tissue, overall polarization information of the sample can be obtained by rotating the polarization angle of the illuminating linearly polarized light and detecting backscattered light of different polarization angles.

The computer fits a functional relation of polarized images of the illuminated region of the sample with the polarization angle of the illuminating linearly polarized light and the detected polarization angles, and thus quantitatively obtains information such as fiber orientation, anisotropy, and scattering properties of the sample, which is displayed as a visible pseudo-color image.

BRIEF DESCRIPTION OF THE DRAWINGS

The present invention will become more fully understood from the detailed description given herein below for illustration only, and thus are not limitative of the present invention, and wherein.

DETAILED DESCRIPTION OF THE INVENTION

First Embodiment

A linearly polarized light imaging device of this embodiment is based on scanning by rotating the polarization angle, and mainly includes an incident arm, a reflecting arm, a sample stage, and an image processing computer.

Figure 1:
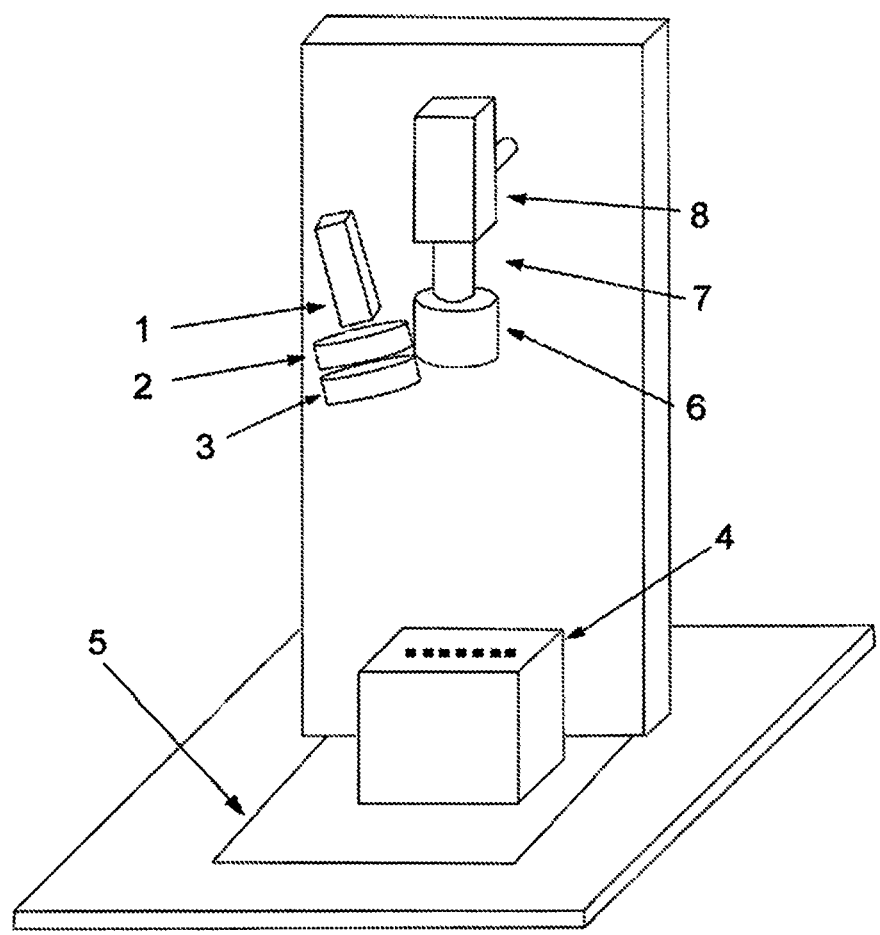
FIG. 1 is a schematic view of a device according to a first embodiment of the present invention.

As shown in FIG. 1, the sample stage 4 is a stage capable of three-dimensional movement, and is used for mounting a sample. The incident arm is disposed on one side of the sample stage, and includes a single-wavelength light source 1, a first polarizing element 2, and an optical system 3 (a lens is used in this embodiment) for generating a parallel light beam. The parallel light beam is incident on a surface of the sample at a fixed angle. The detection arm includes a second polarizing element 6 and a two-dimensional photoelectric detector 8 (a CCD camera is used in this embodiment, in front which a lens 7 may be additionally provided). An output terminal of the two-dimensional photoelectric detector is connected to a corresponding input terminal of the computer. Information of each polarized image of an illuminated region of the sample detected by the two-dimensional photoelectric detector is transmitted to the computer, and the computer stores and processes the information, and generates a pseudo-color image containing information such as fiber orientation, anisotropy, and scattering properties of a biological tissue. In FIG. 1, a light absorbing plate 5 is provided.

A method of rotating the polarization angle of linearly polarized light imaging of the present invention includes the following steps.

Step A: A light beam emitted by a single-wavelength light source is converted into a linearly polarized light beam through a first polarizing element 2, and then the linearly polarized light beam is converted into a parallel light beam; a surface of a sample is illuminated with the parallel light beam, such that backscattered and reflected light passes through a second polarizing element 6; a two-dimensional photoelectric detector 8 records selected linearly polarized light with a certain polarization angle, so as to obtain information of a polarized image of an illuminated region of the sample, and then the information is transmitted to a computer for storage and processing.

Step B: Polarization angles of the first polarizing element 2 and the second polarizing element 6 are scanned from 0° to 180° at a fixed interval, and the two-dimensional photoelectric detector 8 records a polarized image of an illuminated region of the sample corresponding to every combination of the polarization angles of the two polarizing elements. This step corresponds to Step S1 in FIG. 2.

Step S1: The two-dimensional photoelectric detector records continuously to get a series of polarized images, and each image corresponds to an incident polarization angle and a detected polarization angle.

Figure 2:
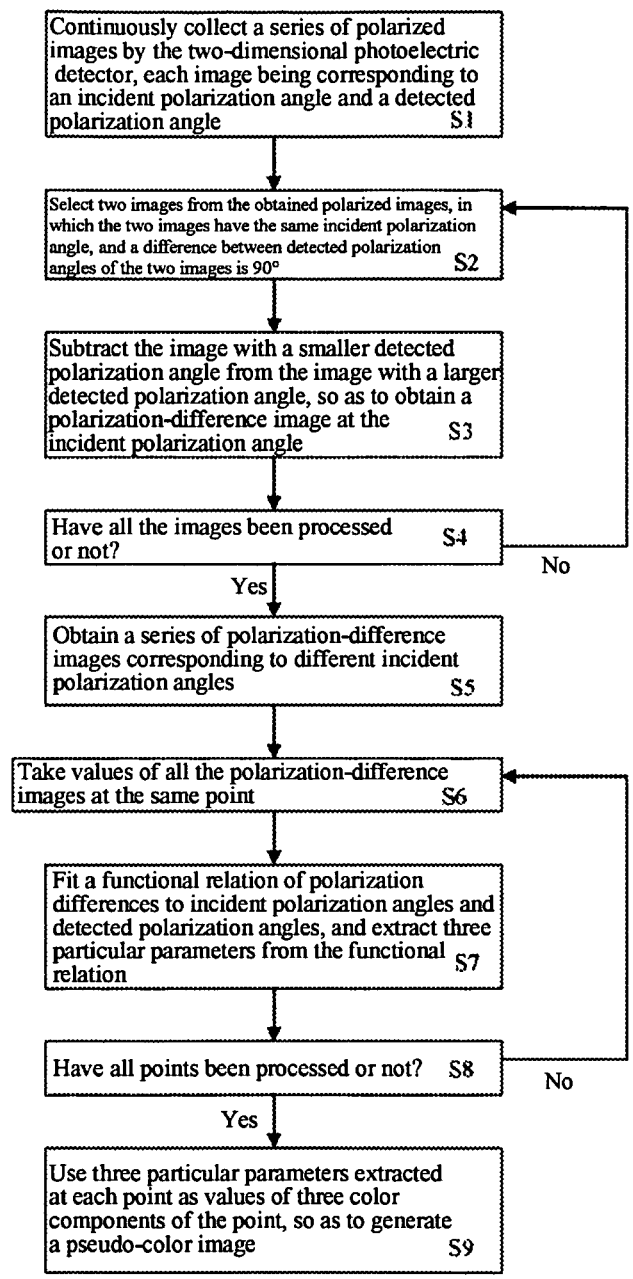
FIG. 2 is a flow chart of calculating and processing all obtained polarized images by a computer according to the first embodiment of the present invention.

Step C: The computer calculates and processes all the obtained polarized images, and generates a pseudo-color image containing information such as fiber orientation, anisotropy, and scattering properties of a biological tissue. As shown in FIG. 2, this step further includes the following steps.

Step S2: Two images are selected from the obtained polarized images, in which the two images have the same incident polarization angle, and a difference between detected polarization angles of the two images is 90°.

Step S3: The image with a smaller detected polarization angle is subtracted from the image with a larger detected polarization angle, so as to obtain a polarization-difference image at the incident polarization angle.

Step S4: Determine whether all the images have been processed or not.

Step S5: If all the images have been processed, a series of polarization-difference images corresponding to different incident polarization angles are obtained.

Step S6: Values of all the polarization-difference images are taken at the same pixel.

Step S7: Fit a functional relation of polarization differences to incident polarization angles and detected polarization angles. And three particular parameters are extracted from the functional relation.

Step S8: Determine whether all pixels have been processed or not.

Step S9: If all pixels have been processed, three particular parameters extracted at each point are used as values of three color components of the pixel, so as to generate a pseudo-color image.

The principle of generating the pseudo-color image is as follows. The functional relation of polarization differences to incident polarization angles and detected polarization angles is composed of several trigonometric functions. It has been found through experimental studies that, magnitudes and phases of the trigonometric functions as well as a ratio of magnitudes of two trigonometric functions respectively represent anisotropy, fiber orientation, and scattering coefficient of a tissue. Therefore, the three are used as particular parameters to serve as components in a red, green, and blue (RGB) color space, so as to generate a pseudo-color image. (However, in addition to the RGB color space, other color spaces such as a YUV color space may also be selected.)

For example, through experiment, a functional relation of an intensity difference between two orthogonal polarized components of detected scattered light to a polarization angle of incident linearly polarized light and a detected polarization angles is obtained as follows.

$$DP(\theta_i, \theta_s) = \lfloor \sqrt{A\cos(4\theta_s - \varphi_1) + B} \rfloor \cos(2\theta_s - \varphi_2(\theta_s)) + C\cos(2\theta_s - \varphi_3)$$

$$\tan(\varphi_2(\theta s)) = D\tan(2\theta_s - \varphi_2) + E$$

$$C < 0, \ A > 0,$$

$$\varphi_1, \varphi_2, \varphi_{3 \in}[0, 2\pi], \varphi_{1 \in}[0, \pi]$$

$\theta_i$ is the polarization angle of the incident linearly polarized light.

$\theta_s$ is the detected polarization angle.

A, B, and C respectively represent contributions of photons of different scattering times to the polarization difference.

As $\phi_1$ is quadruple of a fiber orientation angle, and $$\frac{\phi_3}{2}$$

is equal to the fiber orientation angle, $A/(A+B)$, $C^2/(C^2+B)$, and $|D-1|$ are associated with optical anisotropy of the sample, and $C^2/(C^2+B)$ is also associated with the scattering depolarization of the sample. Three parameters may be extracted from the parameters to serve as three components in an RGB color space, so as to generate a pseudo-color image.

Second Embodiment

Figure 3:
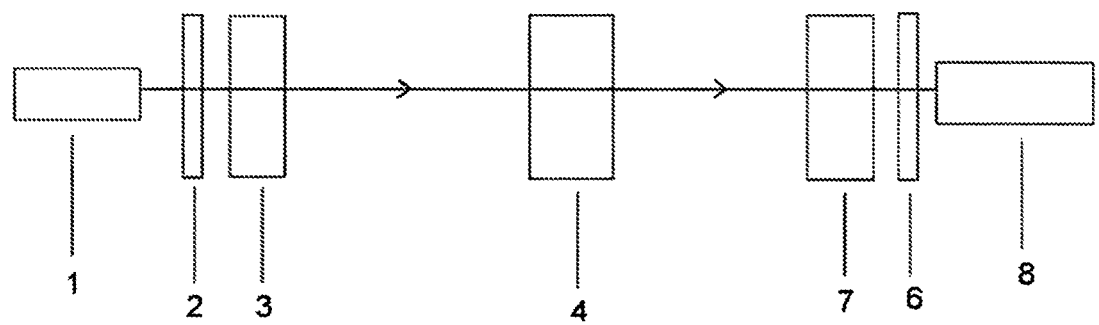
FIG. 3 is a schematic view of a device according to a second embodiment of the present invention.

As shown in FIG. 3, the difference between this embodiment and the first embodiment lies in that, the backward detection mode as described in the first embodiment is not used to record back-reflected light and scattered light of the sample, but instead, a forward detection mode is used to record transmitted light passing through the sample. Other processing methods and experimental methods remain unchanged.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents. For example, the light source 1 is not limited to a single-wavelength light source, and may also be a broad-spectrum light source; the polarization angles of the incident polarized light and the reflected polarized light are not limited to 0° to 180°, and may also be A° to B°, for example, 30° to 300°, as long as a difference between B and A is greater than 180° (one cycle).

What is claimed is:

1. A linearly polarized light imaging device, comprising an incident arm, a detection arm, a sample stage, and an image processing computer, wherein the incident arm comprises a light source and a first polarizing element, and is disposed on one side of the sample stage, incident polarized light of a certain polarization angle passing through the first polarizing element; the detection arm comprises a second polarizing element and a photoelectric detector, and is disposed on a light-detection path on the same or the other side of the sample stage, said photoelectric detector detecting linearly polarized light with certain polarization angles reflected or scattered by or transmitted through a sample on the sample stage, that is, detected polarized light; an output terminal of the photoelectric detector is connected to a corresponding input terminal of the computer; and wherein the imaging device further comprises a polarization angle adjusting device for adjusting polarization angles of the incident polarized light from the first polarizing element and of the detected polarized light from the second polarizing element to obtain a series of polarized images, each image corresponding to an incident polarization angle and a detected polarization angle, wherein the computer processes all the obtained polarized images to obtain information of the sample to be detected through following steps:

S2) selecting two images from the obtained polarized images, wherein the two images have the same incident polarization angle, and a difference between detected polarization angles of the two images is 90°;

S3) subtracting the image with a smaller detected polarization angle from the image with a larger detected polarization angle, so as to obtain a polarization-difference image at the incident polarization angle;

S4) determining whether all the images have been processed or not;

S5) if yes, obtaining a series of polarization-difference images corresponding to different incident polarization angles;

S6) taking values of all the polarization-difference images at the same pixel;

S7) fitting a functional relation of polarization differences to incident polarization angles and detected polarization angles, and extracting three particular parameters from the functional relation;

S8) determining whether all pixels have been processed or not; and

S9) if yes, using the three particular parameters extracted at each pixel as values of three color components of the pixel, so as to generate a pseudo-color image.

2. The linearly polarized light imaging device according to claim 1, wherein the photoelectric detector is a two-dimensional photoelectric detector.

3. The linearly polarized light imaging device according to claim 1, further comprising an optical system for generating a parallel light beam, wherein the optical system is located behind the first polarizing element, and the parallel light beam is incident on a surface of a sample at a fixed angle.

4. The linearly polarized light imaging device according to claim 3, wherein the sample stage is a stage capable of three-dimensional movement.

5. The linearly polarized light imaging device according to claim 1, wherein the light source is a single-wavelength light source.

6. A linearly polarized light imaging method, comprising:

a) illuminating a surface of a sample to be detected using incident linearly polarized light with a certain polarization angle;

b) detecting linearly polarized light with certain polarization angles reflected or scattered by or transmitted through the sample, that is, detected polarized light by a photoelectric detector;

c) adjusting polarization angles of the incident polarized light and the detected polarized light, and repeating the steps a) and b) to obtain a series of polarized images, each image corresponding to an incident polarization angle and a detected polarization angle; and d) processing all the obtained polarized images by a computer to obtain information of the sample to be detected, wherein the step d) of processing all the obtained polarized images by the computer to obtain information of the sample to be detected further comprises:

S2) selecting two images from the obtained polarized images, wherein the two images have the same incident polarization angle, and a difference between detected polarization angles of the two images is 90°;

S3) subtracting the image with a smaller detected polarization angle from the image with a larger detected polarization angle, so as to obtain a polarization-difference image at the incident polarization angle;

S4) determining whether all the images have been processed or not;

S5) if yes, obtaining a series of polarization-difference images corresponding to different incident polarization angles;

S6) taking values of all the polarization-difference images at the same pixel;

S7) fitting a functional relation of polarization differences to incident polarization angles and detected polarization angles, and extracting three particular parameters from the functional relation;

S8) determining whether all pixels have been processed or not; and

S9) if yes, using the three particular parameters extracted at each pixel as values of three color components of the pixel, so as to generate a pseudo-color image.

7. The linearly polarized light imaging method according to claim 6, wherein in the step c), a method for adjusting the polarization angles of the incident polarized light and the detected polarized light comprises scanning from a first angle to a second angle at a fixed interval, and a difference between the second angle and the first angle is greater than 180°.

8. The linearly polarized light imaging method according to claim 6, wherein the three particular parameters in the steps S7) and S9) are fiber orientation, anisotropy, and scattering properties of a biological tissue.

* * * * *